US011833025B2

(12) United States Patent
Ruvalcaba

(10) Patent No.: US 11,833,025 B2
(45) Date of Patent: Dec. 5, 2023

(54) SYSTEMS AND METHODS FOR IMPLANTS AND DEPLOYMENT DEVICES

(71) Applicant: AVANTEC VASCULAR CORPORATION, Sunnyvale, CA (US)

(72) Inventor: Teresa Ruvalcaba, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 338 days.

(21) Appl. No.: 17/135,104

(22) Filed: Dec. 28, 2020

(65) Prior Publication Data

US 2021/0251739 A1   Aug. 19, 2021

Related U.S. Application Data

(63) Continuation of application No. PCT/US2019/039885, filed on Jun. 28, 2019.

(60) Provisional application No. 62/692,260, filed on Jun. 29, 2018.

(51) Int. Cl.
*A61B 17/221* (2006.01)
*A61F 2/01* (2006.01)

(52) U.S. Cl.
CPC ............ *A61F 2/011* (2020.05); *A61B 17/221* (2013.01)

(58) Field of Classification Search
CPC . A61M 25/0074; A61F 2/01–2002/077; A61F 2/95–9/97; A61B 17/221; A61B 2017/2215; A61B 2017/1205–2017/12095; A61B 17/3468; A61B 17/50
See application file for complete search history.

(56) References Cited

U.S. PATENT DOCUMENTS

| | | | |
|---|---|---|---|
| 3,952,737 A | 4/1976 | Kimmell, Jr. | |
| 4,085,743 A | 4/1978 | Yoon | |
| 4,174,715 A | 11/1979 | Hasson | |
| 4,467,802 A | 8/1984 | Maslanka | |
| 4,611,594 A | 9/1986 | Grayhack et al. | |

(Continued)

FOREIGN PATENT DOCUMENTS

| | | | | |
|---|---|---|---|---|
| EP | 1172073 A1 | 1/2002 | | |
| EP | 2497447 A1 * | 9/2012 | ............... | A61F 2/95 |

(Continued)

OTHER PUBLICATIONS

EP, 19824495.6 Extended Search Report, dated Mar. 15, 2022.

(Continued)

*Primary Examiner* — Kathleen S Holwerda
(74) *Attorney, Agent, or Firm* — ONE LLP

(57) ABSTRACT

After a prolonged period in the body, an IVC filter can be substantially absorbed by the body. When this occurs, it can be very difficult and/or dangerous for the patient if the IVC filter is forcibly removed. Thus, it is desirable to have systems and methods for safely abandoning the removal procedure of the IVC filter. Example embodiments of an apparatus for safely abandoning the removal procedure of the IVC filter can include: a sleeve having a lumen and a first hole on a wall of the sleeve; a shaft slidably disposed within the lumen of the sleeve; a flexible distal extension comprising a braid structure with a first opening; and a first lasso encircling a portion of the first opening of the braid.

20 Claims, 11 Drawing Sheets

(56) References Cited

U.S. PATENT DOCUMENTS

| | | |
|---|---|---|
| 4,655,219 A | 4/1987 | Petruzzi |
| 4,723,936 A | 2/1988 | Buchbinder et al. |
| 4,873,978 A | 10/1989 | Ginsburg |
| 4,960,411 A | 10/1990 | Buchbinder |
| 5,011,488 A | 4/1991 | Ginsburg |
| 5,041,093 A | 8/1991 | Chu |
| 5,074,845 A | 12/1991 | Miraki et al. |
| 5,098,440 A | 3/1992 | Hillstead |
| 5,102,415 A | 4/1992 | Guenther et al. |
| 5,370,647 A | 12/1994 | Graber et al. |
| 5,549,626 A | 8/1996 | Miller et al. |
| 5,601,595 A | 2/1997 | Smith |
| 5,653,684 A | 8/1997 | Laptewicz et al. |
| 5,662,671 A | 9/1997 | Barbut et al. |
| 5,746,251 A | 5/1998 | Bullard |
| 5,782,747 A | 7/1998 | Zimmon |
| 5,800,457 A | 9/1998 | Gelbfish |
| 5,814,064 A | 9/1998 | Daniel et al. |
| 5,827,324 A | 10/1998 | Cassell et al. |
| 5,846,251 A | 12/1998 | Hart |
| 5,908,435 A | 6/1999 | Samuels |
| 5,911,734 A | 6/1999 | Tsugita et al. |
| 5,944,728 A | 8/1999 | Bates |
| 6,001,118 A | 12/1999 | Daniel et al. |
| 6,152,946 A | 11/2000 | Broome et al. |
| 6,156,055 A | 12/2000 | Ravenscroft |
| 6,159,230 A | 12/2000 | Samuels |
| 6,203,561 B1 | 3/2001 | Ramee et al. |
| 6,210,370 B1 | 4/2001 | Chi-Sing et al. |
| 6,238,412 B1 | 5/2001 | Dubrul et al. |
| 6,241,738 B1 | 6/2001 | Dereume |
| 6,251,092 B1 | 6/2001 | Qin et al. |
| 6,251,122 B1 | 6/2001 | Tsukernik |
| 6,264,671 B1 | 7/2001 | Stack et al. |
| 6,273,900 B1 | 8/2001 | Nott et al. |
| 6,290,710 B1 | 9/2001 | Cryer et al. |
| 6,306,163 B1 | 10/2001 | Fitz |
| 6,336,934 B1 | 1/2002 | Gilson et al. |
| 6,395,017 B1 | 5/2002 | Dwyer et al. |
| 6,443,972 B1 | 9/2002 | Bosma et al. |
| 6,447,531 B1 | 9/2002 | Amplatz |
| 6,458,151 B1 | 10/2002 | Saltiel |
| 6,485,501 B1 | 11/2002 | Green |
| 6,500,182 B2 | 12/2002 | Foster |
| 6,569,181 B1 | 5/2003 | Burns |
| 6,569,184 B2 | 5/2003 | Huter |
| 6,602,271 B2 | 8/2003 | Adams et al. |
| 6,605,102 B1 | 8/2003 | Mazzocchi et al. |
| 6,632,236 B2 | 10/2003 | Hogendijk |
| 6,645,222 B1 | 11/2003 | Parodi et al. |
| 6,663,652 B2 | 12/2003 | Daniel et al. |
| 6,679,893 B1 | 1/2004 | Tran |
| 6,695,813 B1 | 2/2004 | Boyle et al. |
| 6,699,260 B2 | 3/2004 | Dubrul et al. |
| 6,702,834 B1 | 3/2004 | Bpylan et al. |
| 6,743,247 B1 | 6/2004 | Levinson et al. |
| 6,780,196 B2 | 8/2004 | Chin et al. |
| 6,800,080 B1 | 10/2004 | Bates |
| 6,833,002 B2 | 12/2004 | Stack et al. |
| 6,896,690 B1 | 5/2005 | Lambrecht et al. |
| 6,958,074 B2 | 10/2005 | Russell |
| 7,211,089 B2 | 5/2007 | Kear et al. |
| 7,322,989 B2 | 1/2008 | Teague et al. |
| 7,338,512 B2 | 3/2008 | McGuckin, Jr. et al. |
| 7,377,925 B2 | 5/2008 | Poll |
| 7,491,210 B2 | 2/2009 | Dubrul et al. |
| 7,625,390 B2 | 12/2009 | Hendriksen et al. |
| 7,658,747 B2 | 2/2010 | Forde et al. |
| 7,731,723 B2 | 6/2010 | Kear et al. |
| 7,780,693 B2 | 8/2010 | Brady et al. |
| 7,780,694 B2 | 8/2010 | Palmer et al. |
| 7,837,702 B2 | 11/2010 | Bates |
| 7,993,362 B2 | 8/2011 | Lowe et al. |
| 8,038,704 B2 | 10/2011 | Sherburne |
| 8,043,322 B2 | 10/2011 | Hendriksen et al. |
| 8,163,004 B2 | 4/2012 | Amplatz et al. |
| 8,202,309 B2 | 6/2012 | Styrc |
| 8,273,073 B2 | 9/2012 | Levine et al. |
| 8,298,244 B2 | 10/2012 | Garcia et al. |
| 8,469,969 B2 | 6/2013 | Kear et al. |
| 8,469,970 B2 | 6/2013 | Diamant |
| 8,475,488 B2 | 7/2013 | Cartier et al. |
| 8,512,401 B2 | 8/2013 | Murray, III et al. |
| 8,747,597 B2 | 6/2014 | Rosqueta et al. |
| 8,795,305 B2 | 8/2014 | Martin et al. |
| 9,232,956 B2 | 1/2016 | Bonneau et al. |
| 9,375,333 B1 * | 6/2016 | Aboytes ............ A61B 17/12109 |
| 9,949,816 B2 | 4/2018 | Becking et al. |
| 2001/0044595 A1 | 11/2001 | Reydel et al. |
| 2002/0010476 A1 | 1/2002 | Mulholland et al. |
| 2002/0062135 A1 | 5/2002 | Mazzocchi et al. |
| 2002/0068967 A1 | 6/2002 | Drasler et al. |
| 2002/0169474 A1 | 11/2002 | Kusleika et al. |
| 2002/0193827 A1 | 12/2002 | McGuckin, Jr. et al. |
| 2003/0130680 A1 | 7/2003 | Russell |
| 2003/0176884 A1 | 9/2003 | Berrada et al. |
| 2003/0187474 A1 | 10/2003 | Keegan et al. |
| 2004/0049226 A1 | 3/2004 | Keegan et al. |
| 2004/0073230 A1 | 4/2004 | Mulholland et al. |
| 2004/0093012 A1 | 5/2004 | Cully et al. |
| 2004/0138677 A1 | 7/2004 | Little et al. |
| 2004/0153118 A1 | 8/2004 | Clubb et al. |
| 2004/0181237 A1 | 9/2004 | Forde et al. |
| 2004/0199202 A1 | 10/2004 | Dubrul et al. |
| 2005/0049576 A1 | 3/2005 | Snell et al. |
| 2005/0159770 A1 | 7/2005 | Divani et al. |
| 2005/0182439 A1 | 8/2005 | Lowe |
| 2005/0187570 A1 | 8/2005 | Nguyen et al. |
| 2005/0234502 A1 | 10/2005 | Gilson et al. |
| 2005/0251197 A1 | 11/2005 | Hensley et al. |
| 2005/0267515 A1 | 12/2005 | Oliva et al. |
| 2005/0283166 A1 | 12/2005 | Greenhalgh |
| 2006/0020256 A1 | 1/2006 | Bell et al. |
| 2006/0074410 A1 | 4/2006 | Malecki et al. |
| 2006/0074446 A1 | 4/2006 | Gilson et al. |
| 2006/0184193 A1 | 8/2006 | Lowe et al. |
| 2006/0247572 A1 | 11/2006 | McCartney |
| 2006/0259119 A1 | 11/2006 | Rucker |
| 2007/0005101 A1 | 1/2007 | Fahey et al. |
| 2007/0027520 A1 | 2/2007 | Sherburne |
| 2007/0112374 A1 | 5/2007 | Paul et al. |
| 2007/0129753 A1 | 6/2007 | Quinn et al. |
| 2007/0149996 A1 | 6/2007 | Coughlin |
| 2007/0162048 A1 | 7/2007 | Quinn et al. |
| 2007/0173884 A1 | 7/2007 | Gilson et al. |
| 2007/0186933 A1 | 8/2007 | Domingo et al. |
| 2007/0233223 A1 | 10/2007 | Styrc |
| 2007/0239254 A1 | 10/2007 | Chia et al. |
| 2007/0244504 A1 | 10/2007 | Keegan et al. |
| 2007/0282369 A1 | 12/2007 | Gilson et al. |
| 2008/0091223 A1 | 4/2008 | Pokorney et al. |
| 2008/0269774 A1 | 10/2008 | Garcia et al. |
| 2009/0182370 A1 | 7/2009 | Volobuyev et al. |
| 2009/0192485 A1 | 7/2009 | Heuser |
| 2009/0198315 A1 | 8/2009 | Boudjemline |
| 2009/0222035 A1 * | 9/2009 | Schneiderman ...... A61B 17/221 604/264 |
| 2009/0222076 A1 | 9/2009 | Figulla et al. |
| 2009/0248060 A1 | 10/2009 | Schneider et al. |
| 2009/0287291 A1 | 11/2009 | Becking et al. |
| 2009/0299393 A1 | 12/2009 | Martin et al. |
| 2010/0030254 A1 | 2/2010 | Chanduszko et al. |
| 2010/0030256 A1 | 2/2010 | Dubrul et al. |
| 2010/0057184 A1 | 3/2010 | Randolph et al. |
| 2010/0137846 A1 | 6/2010 | Desai et al. |
| 2010/0256669 A1 | 10/2010 | Harris et al. |
| 2010/0280495 A1 | 11/2010 | Paul et al. |
| 2010/0312268 A1 | 12/2010 | Belson |
| 2010/0331949 A1 | 12/2010 | Habib |
| 2011/0040321 A1 | 2/2011 | Cartier |
| 2011/0046611 A1 | 2/2011 | Christiansen |
| 2011/0125180 A1 | 5/2011 | Tripp et al. |
| 2011/0178547 A1 | 7/2011 | Paul, Jr. et al. |
| 2011/0282274 A1 | 11/2011 | Fulton, III |

(56) References Cited

U.S. PATENT DOCUMENTS

| | | |
|---|---|---|
| 2011/0288572 A1 | 11/2011 | Martin |
| 2011/0307002 A1 | 12/2011 | Gilson et al. |
| 2012/0010699 A1 | 1/2012 | Vesely |
| 2012/0029607 A1 | 2/2012 | McHugo et al. |
| 2012/0041473 A1 | 2/2012 | Nigon |
| 2012/0089216 A1 | 4/2012 | Rapaport et al. |
| 2012/0123515 A1 | 5/2012 | Hosford et al. |
| 2012/0316638 A1 | 12/2012 | Grad et al. |
| 2013/0053882 A1 | 2/2013 | Hocking et al. |
| 2013/0131690 A1 | 5/2013 | Nagl et al. |
| 2013/0184738 A1 | 7/2013 | Laroya et al. |
| 2013/0197567 A1 | 8/2013 | Brady et al. |
| 2013/0253573 A1 | 9/2013 | Agnew |
| 2013/0267848 A1 | 10/2013 | Fearmot et al. |
| 2013/0289694 A1 | 10/2013 | Sherburne |
| 2013/0297010 A1 | 11/2013 | Bishop et al. |
| 2013/0317589 A1 | 11/2013 | Martin et al. |
| 2014/0005712 A1 | 1/2014 | Martin |
| 2014/0024887 A1 | 1/2014 | Ishii et al. |
| 2014/0155930 A1 | 6/2014 | Bennett et al. |
| 2014/0172008 A1 | 6/2014 | McKinnis et al. |
| 2014/0243878 A1 | 8/2014 | Urbanski et al. |
| 2014/0257362 A1 | 9/2014 | Eidenschink |
| 2014/0277089 A1 | 9/2014 | Goode et al. |
| 2014/0309656 A1 | 10/2014 | Gal et al. |
| 2014/0373334 A1 | 12/2014 | Gamarra et al. |
| 2015/0105819 A1 | 4/2015 | Becking et al. |
| 2015/0133918 A1 | 5/2015 | Sachar |
| 2015/0351775 A1 | 12/2015 | Fulton, III |
| 2015/0366650 A1 | 12/2015 | Zi et al. |
| 2016/0081704 A1 | 3/2016 | Jeon et al. |
| 2016/0095689 A1 | 4/2016 | Becking et al. |
| 2016/0095690 A1 | 4/2016 | Becking et al. |
| 2016/0166370 A1 | 6/2016 | DeBeer et al. |
| 2016/0166372 A1 | 6/2016 | Villareal et al. |
| 2016/0228134 A1 | 8/2016 | Martin et al. |
| 2016/0296315 A1 | 10/2016 | Yachia et al. |
| 2017/0014232 A1 | 1/2017 | Ginn et al. |

FOREIGN PATENT DOCUMENTS

| | | |
|---|---|---|
| JP | H 10-509623 A | 9/1998 |
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |
| KR | 101133157 B1 | 4/2012 |
| WO | WO 00/16846 A1 | 3/2000 |
| WO | WO 2007/110864 A2 | 10/2007 |
| WO | WO 2016/025434 A1 | 2/2016 |
| WO | WO 2017/099786 A1 | 6/2017 |

OTHER PUBLICATIONS

CN, 201580067678.4 First Office Action, dated Aug. 28, 2018.
CN, 201480084040.7 Second Office Action, dated Jun. 3, 2019.
EP, 14810754.3 Extended Search Report, dated Nov. 24, 2016.
EP, 14907807.3 Supplementary Search Report, dated May 15, 2018.
EP, 15867928.2 Supplementary Search Report, dated Jun. 5, 2018.
EP, 15867562.9 Supplementary Search Report, dated Jun. 5, 2018.
EP, 16873911.8 Supplementary Search Report, dated May 2, 2019.
EP, 15910402.5 Supplementary Search Report, dated May 13, 2019.
EP, 15910402.5 Extended Search Report, dated Aug. 27, 2019.
EP, 17884666.3 Extended Search Report, dated Jul. 15, 2020.
EP, 19208256.8 Extended Search Report, dated May 18, 2020.
JP, 2016-519686 Office Action, dated Mar. 28, 2018.
JP, 2017-530592 Office Action, dated Sep. 27, 2018.
JP, 2017-530585 Office Action, dated Jul. 16, 2019.
JP, 2018-529531 Office Action, dated Sep. 19, 2019.
WO, PCT/US2014/042343 ISR and Written Opinion, dated Sep. 30, 2014.
WO, PCT/US2015/058898 ISR and Written Opinion, dated Feb. 11, 2016.
WO, PCT/US2015/065074 ISR and Written Opinion, dated Mar. 22, 2016.
WO, PCT/US2015/065025 ISR and Written Opinion, dated Apr. 1, 2016.
WO, PCT/US2015/065102 ISR and Written Opinion, dated Sep. 8, 2016.
WO, PCT/US2017/067343 ISR and Written Opinion, dated Mar. 22, 2018.
WO, PCT/US19/39885 ISR and Written Opinion, dated Sep. 13, 2019.

* cited by examiner

SYSTEMS AND METHODS FOR IMPLANTS AND DEPLOYMENT DEVICES

CROSS-REFERENCE TO RELATED APPLICATIONS

This application is a continuation of PCT Application No. PCT/US19/39885, filed Jun. 28, 2019, which claims the benefit of and priority to U.S. Provisional Application No. 62/692,260 filed Jun. 29, 2018, both of which are incorporated by reference herein in their entireties for all purposes.

FIELD

Various aspects of the disclosure relate to a system and method for implants and deployment devices.

BACKGROUND

Temporary inferior vena cava (IVC) filters are placed much like permanent IVC filters, but are designed so that they may be retrieved in a subsequent endovascular procedure. As the name implies, IVC filters are placed within the IVC—a large vein in the abdomen that returns blood from the lower body to the heart. Patients that need an IVC filter typically have a high risk of having a pulmonary embolism. IVC filters are designed to capture emboli (blood clots) and prevent them from reaching the lung. Temporary IVC filters are typically removed from the patient within 2-3 weeks.

The removal process is generally simple and can be done from the femoral vein or the internal jugular vein. However, complications during the removal process can occur, particularly, when the body has absorbed a portion of the IVC filter and thus making the removal of the IVC filter very difficult. In certain cases, where the IVC filter is substantially absorbed by the body (e.g., tissues enveloping a portion of the IVC filter), a force removal of the IVC filter can be very dangerous to the patient as too much pulling pressure, in the effort to remove the IVC filter, can tear and/or rupture the IVC.

Accordingly, there exists a need to safely abandon the IVC filter removal process when the IVC filter has already been snared and/or captured by the IVC filter capturing device.

SUMMARY

Example embodiments of an apparatus for delivery and/or retrieval of a foreign body are described herein. The foreign body can be a man-made medical device (e.g., a vascular device) or a biological body (e.g., a clot or thrombus). Certain embodiments of the apparatus can include a sleeve, an elongate member received within the sleeve, a flexible distal extension associated with the sleeve, and a tether that passes through a first hole on a wall of the sleeve and at least partially around an opening in the flexible distal extension. The shaft can be configured to hold the tether in place against the sleeve. Various configurations of the apparatus, as well as methods for using and manufacturing the various configurations, are further described herein.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The foregoing summary, as well as the following detailed description, is better understood when read in conjunction with the accompanying drawings. The accompanying drawings, which are incorporated herein and form part of the specification, illustrate a plurality of embodiments and, together with the description, further serve to explain the principles involved and to enable a person skilled in the relevant art(s) to make and use the disclosed technologies.

DETAILED DESCRIPTION

Overview

To better understand the various functions and features of the systems and methods for delivering and/or removing a foreign body, an overview of a delivery and/or removal apparatus (referred to herein as "delivery-removal apparatus") is provided. This overview and many embodiments herein are described in the context of use of the delivery-removal apparatus to retrieve a medical device, namely an inferior vena cava (IVC) filter. However, the delivery-removal apparatus can be used with respect to other foreign bodies such as other medical devices, for example, other vascular filters, vascular occlusion devices, prosthetic devices (e.g., valves), and the like. The delivery-removal apparatus can also be used to retrieve other foreign bodies such as a clot or thrombus from within the vasculature of a subject. The delivery-removal apparatus can be likewise used to deliver man-made medical devices to the body, in the vasculature or otherwise.

Figure 1:
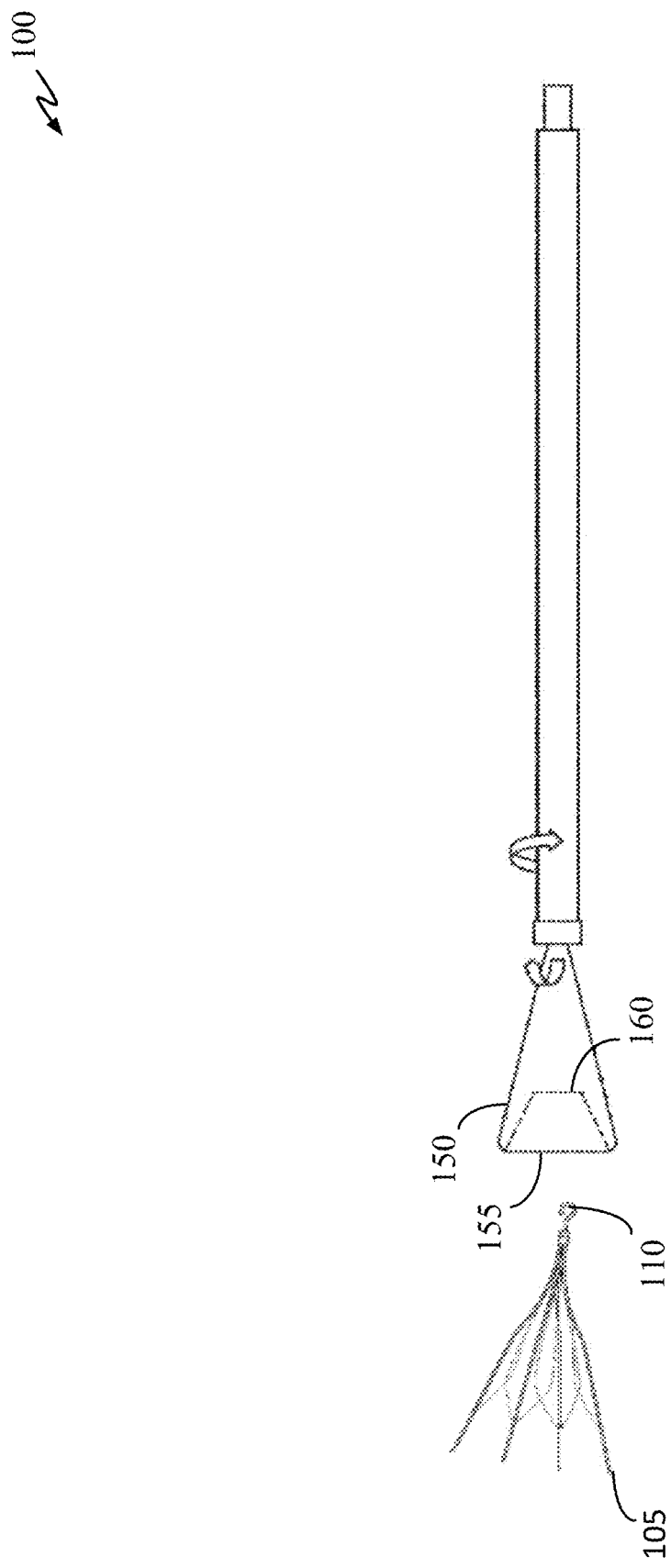
FIG. 1 depicts an example embodiment of a delivery or removal apparatus in accordance with some embodiments of the disclosure.

FIG. 1 illustrates an IVC filter 105 and an IVC filter delivery-removal apparatus 100 in accordance with some embodiments of the present disclosure. IVC filter 105 can be a conventional temporary filter having an enlarged (e.g., hooked) end interface 110 for retrieval. IVC filter 105 can also have a nubbin-type end interface that provides a surface to which apparatus 100 can grab onto and retrieve IVC filter 105. In use, IVC filter 105 is placed within the inferior vena cava to capture any passing emboli. Typically, IVC filter 105 is removed within 2-4 weeks after being installed in the IVC. To remove IVC filter 105, apparatus 100 is used to deliver a funnel-shaped flexible extension 150 into the IVC. The funnel-shaped extension 150 is advanced until it captures or ensnares the end interface of IVC filter 105. Funnel-shaped extension 150 can have one or more openings 155 and 160 to receive end interface 110 of IVC filter 105. Each of the one or more openings of funnel-shaped extension 150 can have a lasso (not shown) encircling a portion (or the entirety) of the one or more openings. In some embodiments, the lasso may have a slipknot. Alternatively, the lasso may not have a slipknot. In place of a lasso, each of the one or more openings can have a tether, a thread, a filament, etc., that can enable the one or more openings to be closed or contracted to a substantially closed position.

To capture IVC filter 105, the end interface of IVC filter 105 is guided into the one or more openings of funnel-shaped extension 150. Once the end interface is advanced inside of the one or more openings (and inside of the funnel), the one or more openings can be closed or tightened by cinching the lasso. This can be accomplished by pulling one of the two ends of the lasso.

With the lasso cinched, IVC filter 105 is captured and can be pulled out of the IVC by retreating funnel-shaped extension 150. This can be done by slowly pulling apparatus 100 entirely out. However, after a prolonged period in the body, an IVC filter can be substantially absorbed by the body (e.g., body tissues can encompass a portion of the IVC filter). When this occurs, it can be very difficult and/or dangerous for the patient if the IVC filter is forcibly removed. Thus, it is desirable to have systems and methods for safely abandoning the removal procedure of the IVC filter.

Delivery-Removal Apparatus

Figure 2:
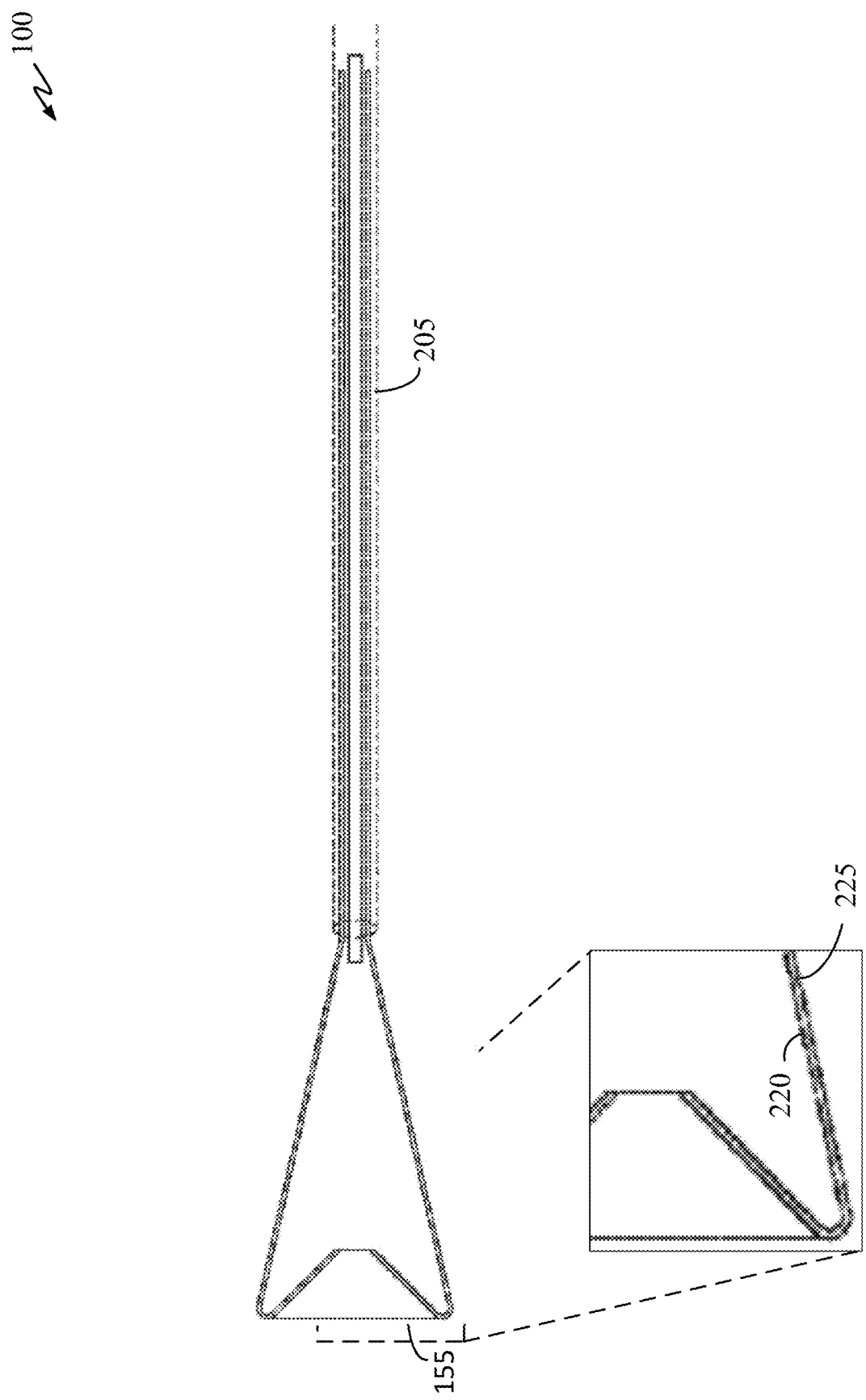
FIG. 2 is a cut-out view of the delivery or removal apparatus in accordance with some embodiments of the disclosure.

FIG. 2 illustrates a side view of IVC filter delivery-removal apparatus 100 in accordance with some embodiments of the present disclosure. Apparatus 100 provides a simple and effective way of abandoning the IVC filter retrieval process by bailing out of the IVC filter capturing process in order to not endanger the patient by forcibly removing an IVC filter that is stuck and/or hardened on the IVC wall. Apparatus 100 can include an outer sleeve 205, an inner sleeve 210, an inner shaft 215, and a funnel-shaped flexible extension 150. Funnel-shaped flexible extension 150 can be bonded to outer sleeve 205 using adhesive, heat, tape, or other means of attachment. Alternatively, flexible extension 150 can be bonded to inner sleeve 210. Funnel-shaped flexible extension 150 can be attached at the distal end of inner sleeve 210, which also has a lumen to receive inner shaft 215. Flexible extension 150 can be composed of any desired material, including metals, alloys, polymers, and composites. In some embodiments, flexible extension 150 is composed of nitinol. Flexible extension can be structurally configured as a sheet, with a lattice structure, as a compilation of struts, or a combination thereof. In some embodiments, flexible extension 150 includes braid. The braid can be arranged in a single layer or with multiple layers, and that single layer, or those multiple layers, can be folded over to form an inner flap.

In the embodiment of FIG. 2, flexible extension 150 includes two layers of braid, an inner braid layer 220 and an outer braid layer 225. In some embodiments, both inner and outer layers 220 and 225 can be bonded to outer sleeve 205. Alternatively, both inner and outer layers 220 and 225 can be bonded to inner sleeve 210. Funnel-shaped flexible extension 150 can have a distal opening 155 and a proximal opening 160.

Figure 3A:
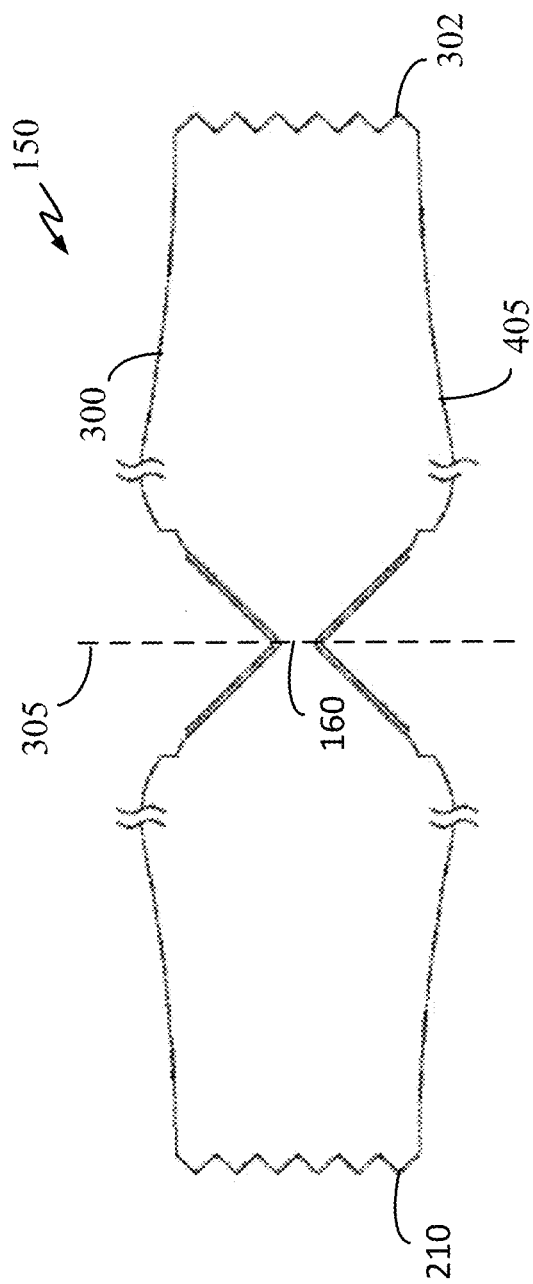
FIG. 3A illustrates the braid tube or cylinder prior it is being folded into a two-layer braid cylinder in accordance with some embodiments of the disclosure.
Figure 3B:
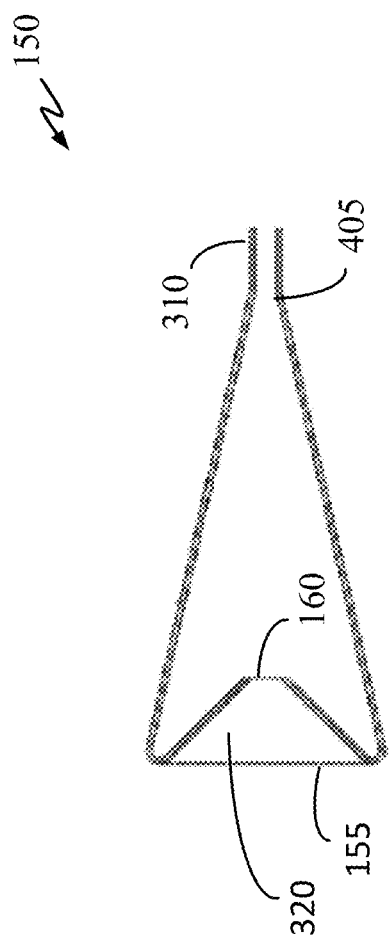
FIG. 3B illustrates the flexible distal extension being formed from the two-layer braid cylinder in accordance with some embodiments of the disclosure.

FIGS. 3A and 3B illustrate one method for fabricating funnel-shaped flexible extension 150 in accordance with some embodiments of the present disclosure. FIG. 3A is a section view of a single-layer braid tube 300 (cylinder). In some embodiments, proximal opening 160 can be formed by folding the single-layer braid tube 300 into itself at axis 305 to form a double-layer braid tube. After the first fold, the double-layer braid tube can have two ends. The first end is proximal opening 160, which is proximal relative to the completed construction of flexible extension 150. The second end 310 (see FIG. 3B) can be bonded to the distal end of inner sleeve 210 or outer sleeve 205. Next, the double-layer tube is folded inwardly such that proximal opening 160 is pushed inward to form a funnel 320 and distal opening 155. In some embodiments, supporting struts (not shown) can be disposed between the layers of the braid. Each strut can extend from the distal end of inner sleeve 210 to the rim of distal opening 155 (between the layers of the braid). Additionally, the supporting struts can be evenly spaced between each other to uniformly support the rim of distal opening 155. Patent application Ser. No. 14/965,500, filed on Dec. 10, 2015, is incorporated herein by reference in its entirety, which discloses in detail the supporting struts as discussed above.

Referring again to FIG. 2, in some embodiments, the entire apparatus 100 (including outer sleeve 205) can be inserted into the IVC. Once in position, outer sleeve 205 can be pulled back to release flexible extension 150 into the IVC. When no longer confined by outer sleeve 205, supporting struts (not shown) can spring open (via shape-memory effect) to open distal opening 155 and form a funnel.

Figure 4:
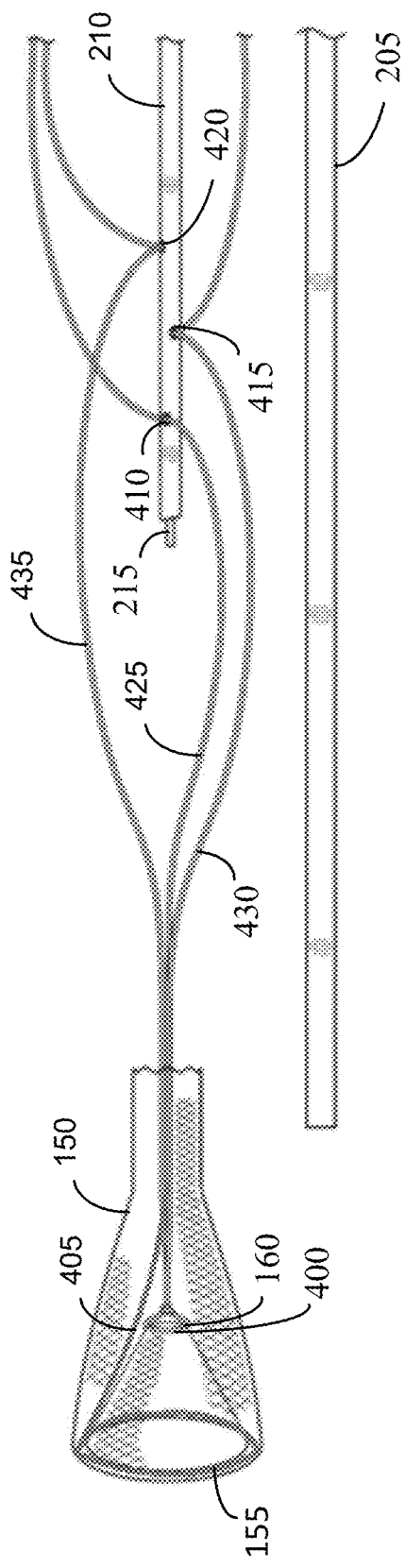
FIG. 4 illustrates an exploded view of the flexible distal extension, the inner shaft, the inner sleeve, and the outer sleeve in accordance with some embodiments of the disclosure.

FIG. 4 illustrates an exploded view of IVC delivery-removal apparatus 100 in accordance with some embodiments of the present disclosure. For ease of illustration, flexible extension 150 is shown detached from outer sleeve 205 or inner sleeve 210. Flexible extension 150 can have two lassos, one for each of the openings. A proximal lasso 400 can encircle the perimeter of proximal opening 160. Proximal lasso 400 can partially or fully encircle the perimeter of proximal opening 160. In some embodiments, a distal lasso 405 can encircle the perimeter of distal opening 155. Distal lasso 405 can partially or fully encircle the perimeter of distal opening 155.

Each of distal and proximal lassos 405 and 400 can be disposed between the layers of the braid, held in position by the compression of the braid layers themselves or by a retainer. In some embodiments, each lasso can be woven such that it interlaces between one or more of the fibers of the braid so that each lasso would stay along the perimeter of its respective opening (e.g., openings 155 and 160).

Inner sleeve 210 can include one or more holes (e.g., holes 410, 415, and 420) on the side wall of inner sleeve 210. In some embodiments, inner sleeve 210 can have one hole. Alternatively, inner sleeve 210 can have two or more holes. Each hole provides an opening for a portion of the lasso to be threaded therethrough. Proximal lasso 400 can have two end sections, a first end section 425, and a second end section 430. In some embodiments, first end section 425 can be threaded through one or more of the holes on inner sleeve 210. Alternatively, first end section 425 can be bonded to the distal portion of inner sleeve 210 using adhesive or other attaching mechanism. A second end section 430 of proximal lasso 400 can be threaded through any of the holes (e.g., hole 410, 415, or 420) of inner sleeve 210.

As shown, first and second end sections 425 and 430 are threaded through at least one of the holes from the outside of inner sleeve 210. Alternatively, first and second ends sections 425 and 430 can be threaded from inside of the lumen of inner sleeve 210. In other words, second end section 430 of proximal lasso 400 can go from the inside to the outside of inner sleeve 210 via hole 415 as opposed to being threaded from the outside to the inside as shown in FIG. 4. Once threaded through hole 415, a portion of second end section 430 can be partially or fully wrapped (e.g., one or more times) around inner shaft 215 before being threaded out of hole 415 again or being threaded out a different hole (e.g., hole 410 or 420). The advantages of threading through a different hole is that the length of second end portion 430 running between the entry hole and the exit hole provides additional contact surface area. This increases friction and holding strength. In some embodiments, a portion of first end section 425 can be partially wrapped or fully wrapped around inner shaft 215 before being threaded out of hole 410 or being threaded out a different hole (e.g., hole 415 or 420).

End section 435 of distal lasso 405 can be threaded through hole 420 of inner sleeve. Alternatively, end section 435 can be threaded through hole 410 or 415. Each hole can have one or more end portions (e.g., end section 425, 430, and/or 435) being threaded therethrough. Distal lasso 405 can have a second end portion (not shown) being attached to the distal end of inner sleeve 210.

Figure 5:
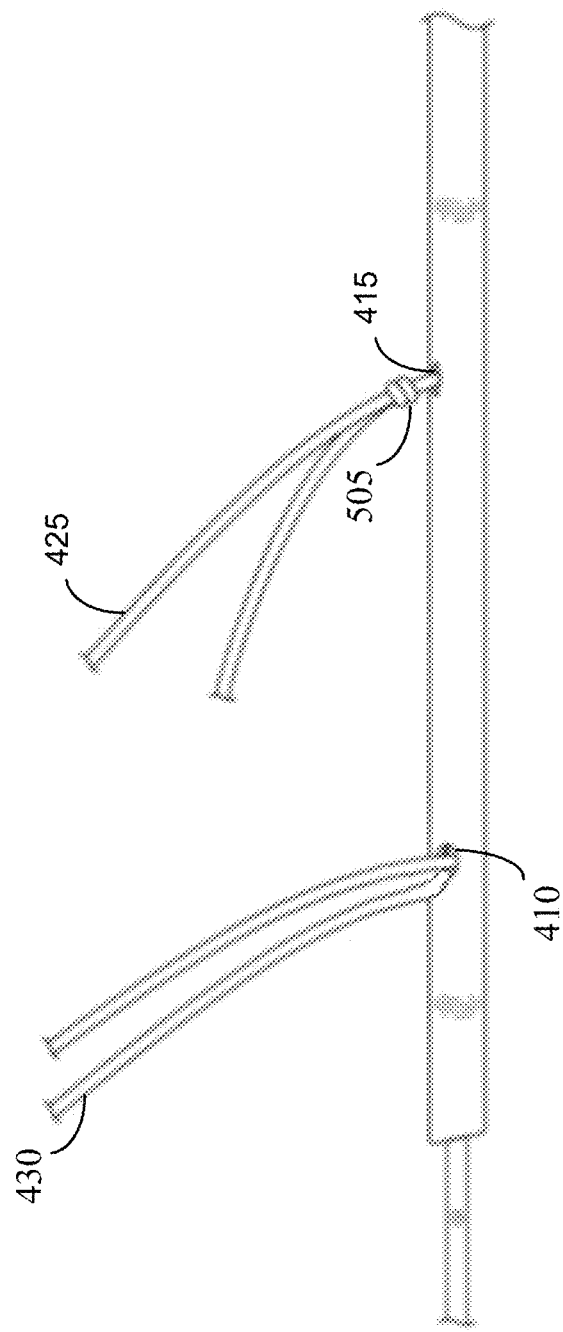
FIGS. 5 and 6 illustrate how one or more end portions of a lasso can be threaded through and/or secured to the inner shaft of the delivery or removal apparatus in accordance with some embodiments of the disclosure.

FIG. 5 is a close up view illustrating how proximal lasso 400 can be threaded through one or more holes of inner sleeve 210 in accordance with some embodiments of the present disclosure. In some embodiments, rather than being bonded or attached to inner sleeve 210, first end section 425 of proximal lasso 400 can be threaded through one of the holes of inner sleeve 210, such as hole 415 (or alternatively hole 410). First end section 425 can be secured in place by partially or fully wrapping around inner shaft 215. In some embodiments, first end section 425 can be wrapped one or more times around inner shaft 215 after being threaded through hole 415. Additionally, first end section 425 can be tied off (knot 505) upon exiting hole 415. After being threaded through hole 415 from the outside, first end section 425 can wrap around inner shaft 215 and exit the same hole 415. Alternatively, first end section 425 can exit a different hole such as hole 410 or hole 420 (see FIG. 4).

In some embodiments, first end section 425 can first be threaded through the lumen of inner sleeve 210 and through one of the holes (e.g., hole 410 or 415) from inside the lumen of inner sleeve 210. Before exiting through one of the holes, first end section 425 can be wrapped partially or fully around inner shaft 215. Upon being threaded through one of the holes, first end section 425 can be tied off or be threaded back into the lumen of inner sleeve 210 at the same hole or at a different hole. This allows first end section 425 to be securely attached to inner shaft 215 via friction forces as first end section 425 is being pushed against the interior wall of inner sleeve 210.

In some embodiments, one of the end portions (e.g., first end section 425) of each lasso can be secured to inner shaft 215 and the other end portion (e.g., second end portion 430) is threaded through one of the holes of inner shaft 215. For example, one of the end portions of each lasso can be securely knotted or tied to inner shaft 215 via one of the holes on inner sleeve 210. The other end portion can be removably secured between inner shaft 215 and inner sleeve 210. Second end portion 430 can be secured to inner sleeve 210 as long as inner shaft 215 remains within the lumen of inner sleeve 210. In other words, second end portion 430 can be held in place by means of it being between inner shaft 215 and inner sleeve 210. When second end portion 430 is between inner shaft 215 and inner sleeve 210, inner shaft 215 pushes second end portion 430 against the interior wall of inner sleeve 210. This secures second end portion 430 until inner shaft 215 is retracted. To increase the friction force between second end portion 430, inner shaft 215, and the interior wall of inner sleeve 210, second end portion 430 can be partially or fully wrapped around inner shaft 215. This provides more surface area of second end portion 430 to be pressed against inner sleeve 210.

As shown in FIG. 5, second end portion 430 can be threaded through hole 410 (or alternatively hole 415 or hole 420 of FIG. 4) from the outside of inner sleeve 210. In some embodiments, second end portion 430 is partially or entirely wrapped around inner shaft 215 prior to exiting out of same hole 410. Second end portion 430 can be wrapped around one or more times around inner shaft 215. In another embodiments, after wrapping around inner shaft 215, second end portion can exit another hole such as hole 415.

The diameters of inner sleeve 210 and shaft 215 are sized such that shaft 215 can freely move about the axial direction of inner sleeve 210. Additionally, the diameters of inner sleeve 210 and shaft 215 may be selected such that inner shaft 215 would tightly press against first end section 425 against the inner wall of inner sleeve 210. In this way, the first end section 425 is tightly secured via friction effect.

Figure 6:
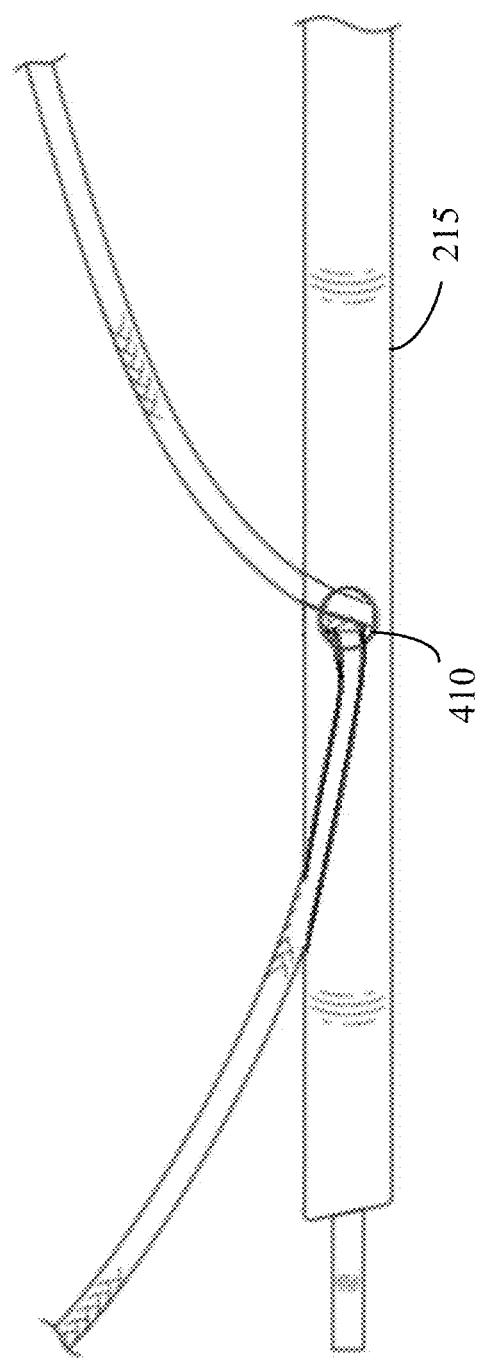

FIG. 6 illustrates inner shaft 215 having a single hole for securing an end portion of a lasso (e.g., proximal lasso 400 or distal lasso 405) in accordance with some embodiments of the present disclosure. As previously mentioned, inner shaft 215 can have one or more holes for securing an end portion of a lasso. In some embodiments, inner shaft 215 can have one hole (e.g., hole 410). An end portion of a lasso can be threaded through hole 410 from the outside (as shown) and exit the same hole once the end portion is partially or fully wrapped around inner shaft 215. In some embodiments, the end portion can enter hole 410 from the inside of inner sleeve 210 rather than from entering from the outside of inner sleeve 210.

Figure 7:
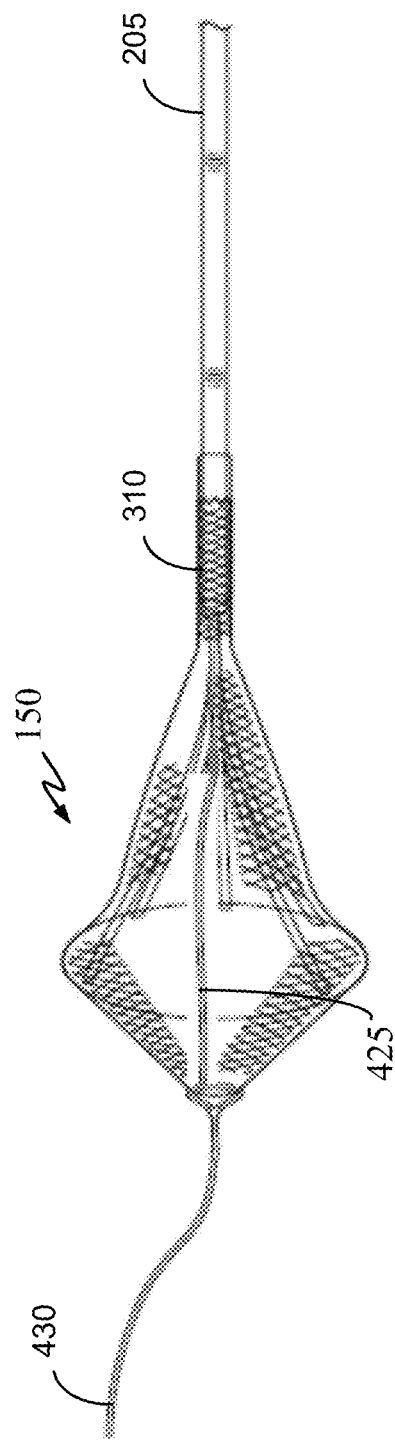
FIG. 7 illustrates an everted flexible distal extension in accordance with some embodiments of the disclosure.

FIG. 7 illustrates flexible extension 150 being everted upon the release of one or more end portions of a lasso in accordance with some embodiments of the present disclosure. As shown, a second end portion 430 of proximal lasso 400 is released as inner shaft 215 (not shown) is retracted. Once second end portion 430 is no longer held between inner shaft 215 and inner sleeve 210, second end portion 430 is free to move and is pulled out of inner sleeve 210 as apparatus 100 is pulled back. This motion results in the eversion of flexible extension 150. In some embodiments, only one of the end portions (e.g., second end portion 430) is released as inner shaft 215 is retracted. The other end portion (e.g., first end section 425) can still be attached or bonded to the distal end of inner sleeve 210. In some embodiments, both end portions can be threaded through one or more holes of inner sleeve 210 and both end portions can be released once inner shaft 215 is retracted. The release of one or more end portions causes flexible extension 150 to evert as proximal lasso 400 is no longer cinching proximal opening 160 and holding it in the inverted position.

Figure 8A:
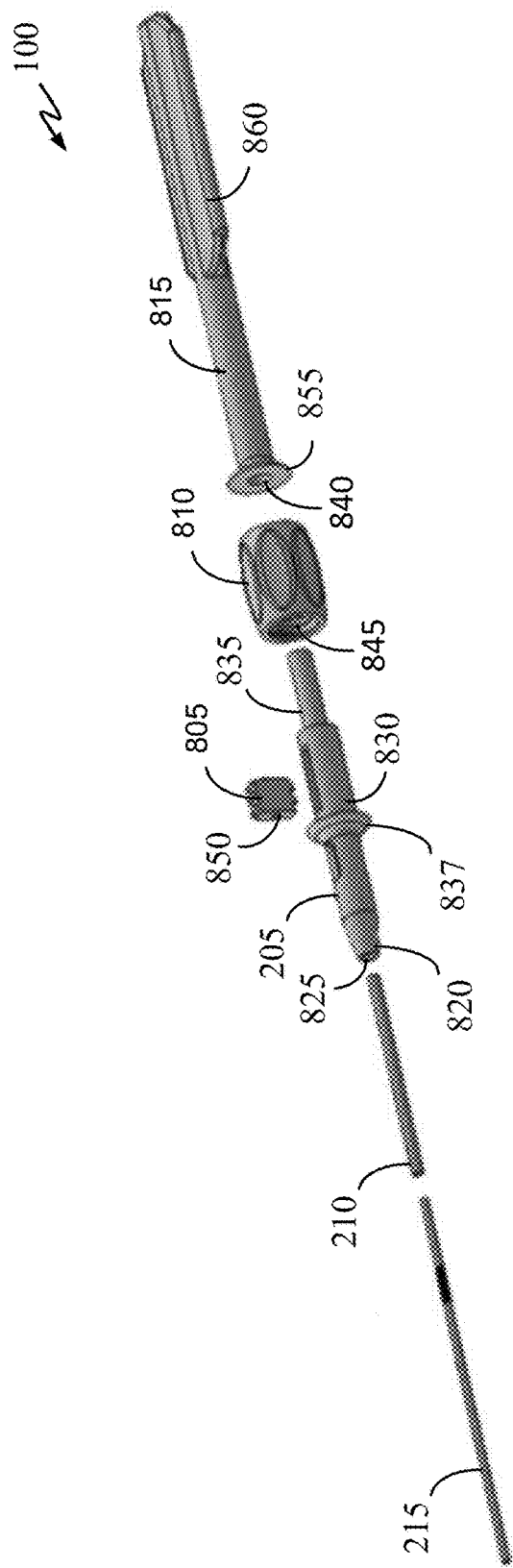
FIG. 8A is an exploded view of the delivery or removal apparatus in accordance with some embodiments of the disclosure.
Figure 8B:
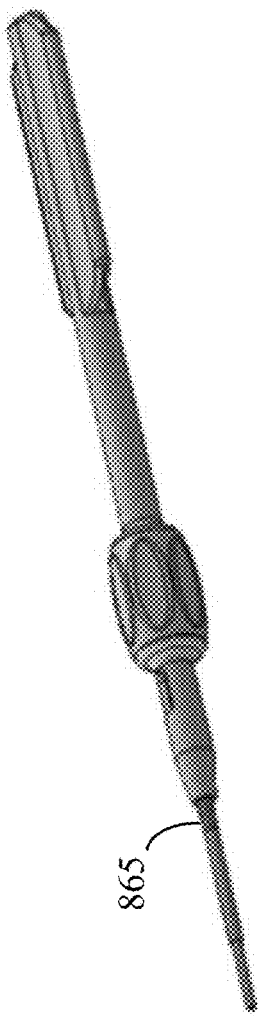
FIG. 8B is a fully assembled view of the delivery or removal apparatus in accordance with some embodiments of the disclosure.

FIG. 8A is an exploded view of apparatus 100 (without flexible extension 150) in accordance with some embodiments of the present disclosure. Apparatus 100 includes outer sleeve 205, inner sleeve 210, inner shaft 215, a cam 805, a knob 810, and a handle 815. Outer sleeve 205 can have a conical distal end 820 and a lumen 825 to receive inner sleeve 210, which can be secured within lumen 825 of outer sleeve 205 using adhesive (865 of FIG. 8B). Outer sleeve 205 can also have a mid-portion 830 with a larger lumen or internal opening (not shown) to house cam 805. Mid-portion 830 can have a flange 837 to keep knob 810 in position once it is inserted over mid-portion 830. The outer diameter of proximal portion 835 of outer sleeve 205 can be smaller than mid-portion 830. In this way, proximal portion 835 can be inserted into a lumen 840 of handle 815. In some embodiments, handle 815 can have a removable cap, such as a screw cap (not shown), on the proximal end, which provides the operator access to pull back inner shaft 215 to release the IVC filter.

Knob 810 includes inner threads (not shown) on the wall of lumen 845. The inner threads of knob 810 mate with the threads on cam 805. As knob 810 turns, cam 805 is translated along the axial direction of outer sleeve 205. For example, cam 805 can be translated toward handle 815 by rotating knob 810 in one direction and can be translated toward distal end 820 by rotating knob 810 in another direction. The directions of rotation and axial movement depend on the thread direction of the threads (i.e., left or right handed threads). Inner shaft 215 can be secured to cam 805 at opening or hole 850. Adhesive can be used to tightly secure inner shaft 215 to cam 805. In this way, when cam 805 is translated inner shaft 215 will also be translated. In some embodiments, the translation motion of inner shaft 215 can pull one or more end portions of one or more lassos toward the proximal direction (which is toward handle 815). This motion can cause distal opening 155 and/or proximal opening 160 to become smaller or substantially closed as one of the end portions of the lasso (e.g., proximal lasso 400 or distal lasso 405) is pulled toward the proximal direction. In this way, end interface 110 of IVC filter 105 can be captured and secured by flexible extension 150.

Figure 9A:
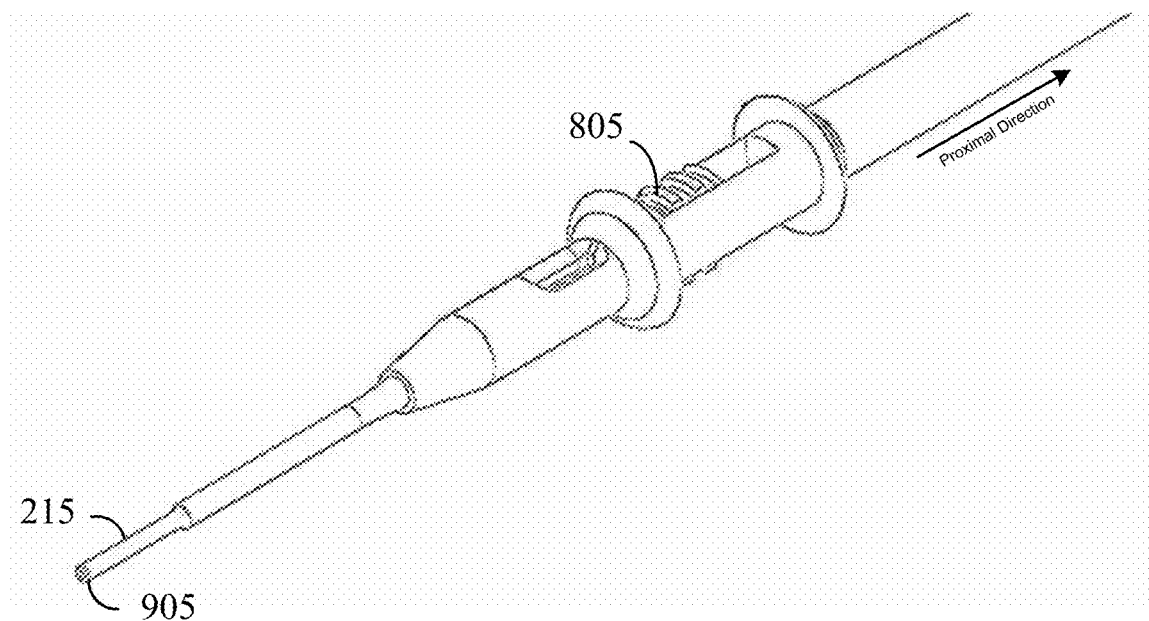
FIGS. 9A and 9B are close up view (without the knob) in accordance with some embodiments of the disclosure.
Figure 9B:
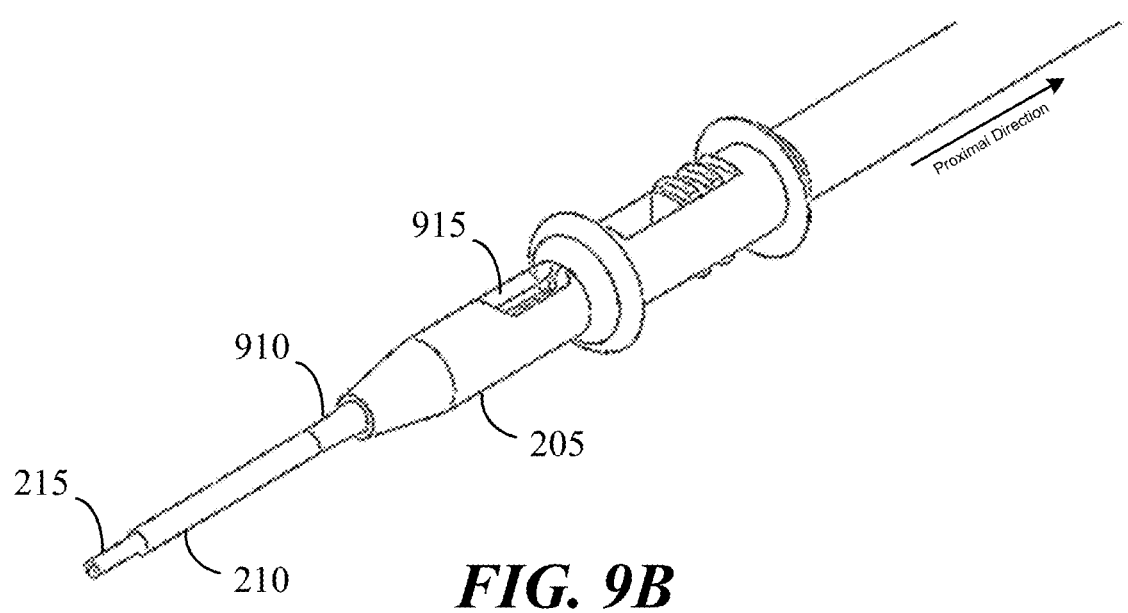

Referring now to FIGS. 9A and 9B, which illustrate the translations of cam 805 (and thereby inner shaft 215) in accordance with some embodiments of the present disclosure. FIG. 9A illustrates cam 805 in the starting position where distal end 905 of inner shaft 215 is in a position closest to the distal end of apparatus 100, which is near the IVC filter when apparatus 100 is inside the IVC during a retrieval procedure. FIG. 9B illustrates cam 805 in the final position, after being translated by the rotation movements of knob 810 (not shown here, see FIG. 8B). As shown, cam 805 has moved axially toward the proximal direction. This translation motion of cam 805 also moves inner shaft 215 toward the proximal direction. In other words, inner shaft 215 is retracted into inner sleeve 210 as cam 805 is axially translated toward the proximal direction. Inner sleeve 210 remains securely stationary as it can be adhesively affixed to outer sleeve 205 using an adhesive 1010. Other means of securely affixing inner sleeve 210 to outer sleeve 205 can be employed such as tape or friction by sizing outer sleeve 210 and the lumen of outer sleeve 205 appropriately to achieve a substantially tight fit.

In some embodiments, outer sleeve 205 can include a window or slot 915. Inner sleeve 210 can be appropriately sized to have a length such that it would not span the entire length of window 915. In this way, inner shaft 215 can be visible through window 915 and thereby allow the operator to confirm the translation of inner shaft 215. In some embodiments, inner shaft 215 can be marked or edged with a visible marking (not shown) to enable the operator to confirm that inner shaft 215 has been axially translated.

Referring again to FIG. 8A, handle 815 can include a flange 855 along the circumference of handle 815. Once knob 810 is inserted over mid-portion 830 and proximal portion 835 is inserted into lumen 840, flanges 837 and 855 keep knob 810 in place. Handle 815 can also include flanges 860, which provide additional surface areas for handling apparatus 100. Additionally, flanges 860 provide an area for the operator to hold and pull handle 815 completely away from proximal portion 835. In other words, proximal portion 835 is no longer within lumen 840 of handle 815.

Figure 10A:
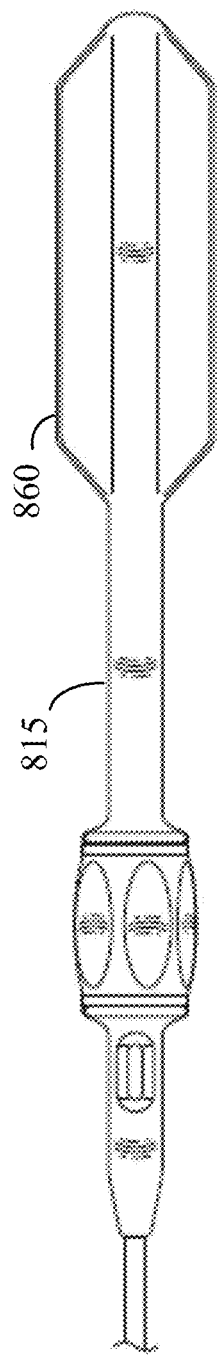
FIG. 10A illustrates a fully assembled delivery or removal apparatus in accordance with some embodiments of the disclosure.
Figure 10B:
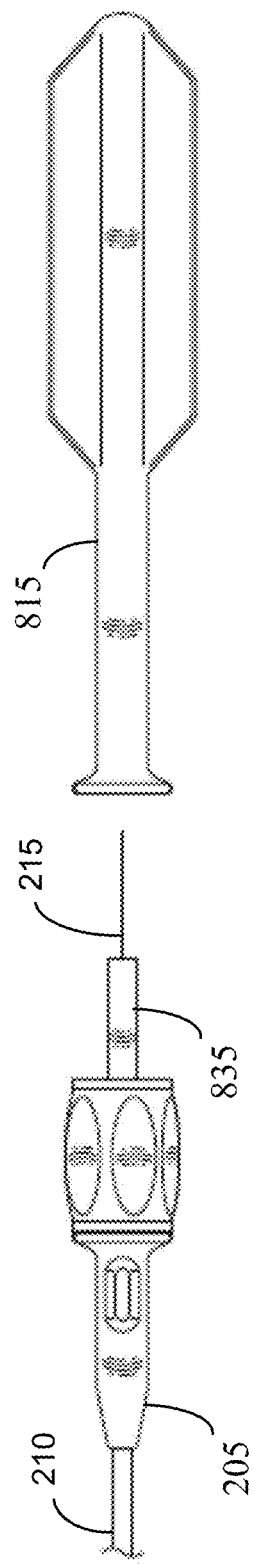
FIG. 10B illustrates a fully assembled delivery-removal apparatus with its handle removed in accordance with some embodiments of the disclosure.

FIG. 10A illustrates apparatus 100 fully assembled. FIG. 10B illustrates handle 815 being pulled away and out of proximal portion 835 of outer sleeve 205. As previously stated, complications can occur during the IVC filter retrieval process. If the retrieval process needs to be abandoned, in some embodiments, handle 815 can be completely pulled away from outer sleeve 205. This procedure exposes inner shaft 215, which is appropriately sized such that it extends beyond proximal portion 835. To abandon the IVC filter retrieval process, inner shaft 215 can be manually pulled out. Inner shaft 215 can be partially or entirely pulled out of inner sleeve 210 and outer sleeve 205. The complete retraction of inner shaft 215 enables one or more end portions (e.g., end portions 425, 430, and 435) of one or more lassos to be freed from the confinement of inner sleeve 210. This allows proximal opening 160 of flexible extension 150 to be everted once inner sleeve 210 is pulled out of the IVC. This can be achieved by pulling outer sleeve 205 away from the patient. In some embodiments, distal opening 155 can get larger as distal lasso 405 is freed.

Figure 11:
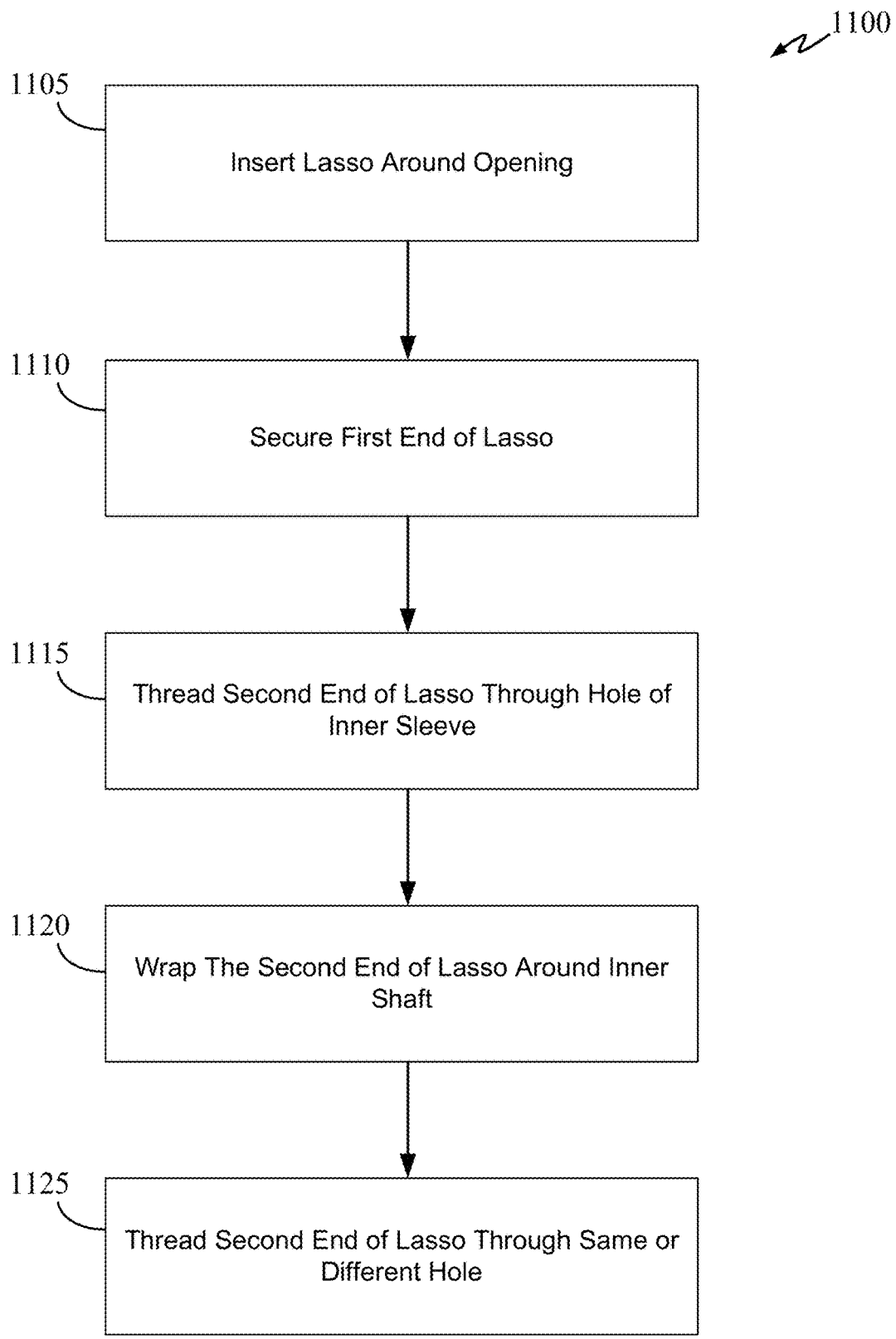
FIG. 11 is a flow diagram on how to fabricate or manufacture a portion of the delivery or removal apparatus in accordance with some embodiments of the disclosure.

FIG. 11 is a flow diagram of a manufacturing process 1100 for fabricating a portion of apparatus 100 in accordance with some embodiments of the present disclosure. Process 1100 starts at 1105 where a lasso is inserted between the two layers of the braid of flexible extension 150. For example, proximal lasso 400 (see FIG. 4) can be disposed between inner layer 220 and outer layer 225 at proximal opening 160. Proximal lasso 400 can partially or fully encircle the circumference of proximal opening 160. Proximal lasso 400 can interweave between one or more of the layers of the braid. This ensures that proximal lasso 400 stays in place (along the rim of proximal opening 160).

Each lasso (e.g., proximal lasso 400 or distal lasso 405) can have two end portions. The first end portion of each lasso can be secured (at 1110) to the distal portion of inner sleeve 210 using adhesive or other attachment methods such as tape. Alternatively, the first end portion of each lasso can be threaded through a hole (e.g., hole 410, 415, or 420) on inner sleeve 210, wrapped partially or entirely around inner shaft 215, threaded through the same hole or a different hole, and finally tied off with a knot. This secures the first end portion in place.

At 1115, the second end portion (e.g., portion 425, 430, or 435) of each lasso can be threaded through one of the holes (e.g., hole 410, 415, or 420) of inner shaft 210. The second end portion can be threaded through one of the holes from the outside or inside of inner sleeve 210. In some embodiments, the second end portion is threaded from the outside of inner sleeve 210. At 1120, the second end portion can be partially or fully wrapped one or more times around inner shaft 215. Wrapping the second end portion around inner shaft 215 increase the contact surface area between the surfaces of inner shaft 215 and the lasso portion. In this way, adequate friction force can be generated to hold the lasso in place.

At 1125, the second end portion can be threaded through a hole again once it is wrapped (partially or fully) around inner shaft 215. The second end portion can be threaded through the same hole or to a different hole. For example, if the second end portion was threaded through hole 410 at 1115, it can be re-threaded to the same hole 410 or to a different hole such as hole 420. The advantages of threading through a different hole is that the length of the second portion running between the entry hole and the exit hole provides additional contact surface area. This increases friction and holding strength.

The embodiments described herein are restated and expanded upon in the following paragraphs without explicit reference to the figures. In many embodiments, an apparatus for delivery or retrieval of a foreign body is provided, the apparatus including: a sleeve having a lumen and a first hole on a wall of the sleeve; a shaft slidably received within the lumen of the sleeve; a flexible distal extension including a braid with a first opening; and a first lasso encircling a portion of the first opening of the braid. The first lasso can have a first and a second end. The first end can be coupled to the sleeve. A proximal portion of the second end can be passed through the first hole and at least partially wrapped around the shaft. In this way, the shaft can hold the second end of the first lasso in place against the sleeve with an interference fit. Further, the flexible distal extension can be coupled to the sleeve.

In some embodiments, the proximal portion of the second end can be partially wrapped around the shaft. Alternatively, the proximal portion of the second end can be fully wrapped around the shaft. The proximal portion of the second end can exit the first hole, from inside of the sleeve, after wrapping around a portion of the shaft.

In some embodiments, the proximal portion of the second end is threaded through the first hole from outside of the sleeve. Alternatively, the proximal portion of the second end can be threaded through the first hole from inside of the sleeve.

The sleeve can also have two or more holes. In some embodiments, the sleeve can have a second hole on the wall of the sleeve. The proximal portion of the second end can be threaded through the first hole from outside of the sleeve and through the second hole from inside of the sleeve. Alternatively, the proximal portion of the second end can be threaded through the first hole from inside of the sleeve and through the second hole from outside of the sleeve.

The braid structure can have two layers, which can be constructed by folding back at a first fold to form two layers. Next, the two layers can be folded back inwardly at a second fold such that the first fold forms a proximal opening of a funnel and the second fold forms a distal opening of the funnel. The first opening of the flexible distal extension can be the same as the distal opening, and the first lasso can be embedded between the two layers of the braid. The first lasso can partially or entirely encircle the distal opening, and can be interweaved between the layers of the braid.

In some embodiments, the apparatus includes a second lasso encircling the proximal opening of the braid. A first end of the second lasso can be coupled to the sleeve, and a second end of the second lasso can be threaded through the first opening of the sleeve—from the inside or outside of the sleeve.

In yet another embodiment, a method for manufacturing a delivery-removal apparatus is described herein. The method includes encircling a lasso at a proximal opening of a funnel shaped extension of the delivery-removal apparatus and securing the first end of the lasso to an inner sleeve of the medical device. The inner sleeve can include a lumen and a first hole on the sidewall of the inner sleeve. The method further includes threading the second end of the lasso through the first hole on the inner sleeve; inserting an inner shaft within the lumen of the sleeve; and wrapping the second end of the lasso around the inner shaft to secure the second end of the lasso.

In many embodiments, an apparatus for delivery or retrieval of a foreign body is provided, the apparatus including: a sleeve having a lumen and a first hole in a wall of the sleeve; an elongate member slidably received within the lumen of the sleeve; a flexible distal extension with a first opening, the flexible distal extension being coupled to the sleeve; and a tether at least partially around a portion of the first opening of the flexible distal extension, where a first end of the tether can be coupled to the sleeve, where a portion of a second end of the tether passes through the first hole and around the shaft, and where the shaft can be configured to hold the second end of the first tether against the sleeve with an interference fit.

In some embodiments, the portion of the second end can be partially wrapped around the shaft. In some embodiments, the portion of the second end can be fully wrapped around the shaft.

In some embodiments, the portion of the second end exits the first hole after wrapping around a portion of the shaft.

In some embodiments, the portion of the second end passes through the first hole from outside of the sleeve. In other embodiments, the portion of the second end passes through the first hole from inside of the sleeve.

In some embodiments, the sleeve further includes a second hole on the wall of the sleeve, where the portion of the second end passes through the first hole from outside of the sleeve and through the second hole from inside of the sleeve.

In some embodiments, the sleeve further includes a second hole on the wall of the sleeve, where the portion of the second end passes through the first hole from inside of the sleeve and through the second hole from outside of the sleeve.

In some embodiments, the flexible distal extension can be folded back to form a flap with a distal opening and a proximal opening, where the first opening can be the distal opening of the flap. The flexible distal extension can include two layers, and the tether can be between the two layers.

In some embodiments, the tether can be a first tether, and the apparatus can further include a second tether at least partially around a proximal opening of the flexible distal extension. A first end of the second tether can be coupled to the sleeve, and a second end of the second tether lasso passes through the first opening of the sleeve.

In some embodiments, the apparatus can further include: a cam coupled to the elongate member; and an interface coupled to the cam, where the cam can be configured to move the inner shaft in an axial direction when the interface is moved.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In many instances, entities are described herein as being coupled to other entities. It should be understood that the terms "coupled" and "connected" (or any of their forms) are used interchangeably herein and, in both cases, are generic to the direct coupling of two entities (without any non-negligible intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a," "an," and "the" include plural referents unless the context clearly dictates otherwise.

The examples and embodiments provided herein are provided for illustrative purposes and are not intended to limit the application or claims provided herein. It will be understood that the specific embodiments disclosed herein and the systems, components, methods, etc. described herein need not take the specific form described, but can instead be applied in various different or additional manners consistent with the present disclosure and claims. It will further be understood that the present disclosure need not take the specific form explicitly described herein, and the present disclosure is intended to include changes variations thereof, consistent with the appended claims and the present disclosure, for example, to optimize the subject matter described herein. The disclosed subject matter is not limited to any single or specific embodiment described herein, but rather should be construed in breadth and scope in accordance with the appended claims.

The invention claimed is:

1. An apparatus for delivery or retrieval of a foreign body, the apparatus comprising:
   a sleeve having a lumen and a first hole on a wall of the sleeve;
   a shaft slidably disposed within the lumen of the sleeve;
   a flexible distal extension comprising a braid with a first opening, the flexible distal extension being coupled to the sleeve; and
   a first lasso encircling a portion of the first opening of the braid, wherein the first lasso comprises a first and a second end, the first end is coupled to the sleeve, a proximal portion of the second end is threaded through the first hole and is wrapped around the shaft, and wherein the shaft holds the second end of the first lasso in place against the sleeve with an interference fit.

2. The apparatus of claim 1, wherein the proximal portion of the second end is partially wrapped around the shaft.

3. The apparatus of claim 1, wherein the proximal portion of the second end is fully wrapped around the shaft.

4. The apparatus of claim 1, wherein the proximal portion of the second end exits the first hole after wrapping around a portion of the shaft.

5. The apparatus of claim 1, wherein the proximal portion of the second end is threaded through the first hole from outside of the sleeve.

6. The apparatus of claim 1, wherein the proximal portion of the second end is threaded through the first hole from inside of the sleeve.

7. The apparatus of claim 1, wherein the sleeve further comprises a second hole on the wall of the sleeve, wherein the proximal portion of the second end is threaded through the first hole from outside of the sleeve and through the second hole from inside of the sleeve.

8. The apparatus of claim 1, wherein the sleeve further comprises a second hole on the wall of the sleeve, wherein the proximal portion of the second end is threaded through the first hole from inside of the sleeve and through the second hole from outside of the sleeve.

9. The apparatus of claim 1, wherein the braid is folded back at a first fold to form two layers, the two layers folded back inwardly at a second fold such that the first fold forms a proximal opening of a funnel and the second fold forms a distal opening of the funnel.

10. The apparatus of claim 9, wherein the first opening is the distal opening and the first lasso is embedded between the two layers of the braid.

11. The apparatus of claim 10 further comprising a second lasso encircling the proximal opening of the braid, wherein a first end of the second lasso is coupled to the sleeve, and a second end of the second lasso is threaded through the first opening of the sleeve.

12. The apparatus of claim 10 further comprising:
   a cam coupled to the shaft; and
   a rotating knob connected to the cam, wherein the cam is configured to move the shaft in an axial direction when the knob is rotated.

13. An apparatus for delivery or retrieval of a foreign body, the apparatus comprising:
   a sleeve having a lumen and a first hole in a wall of the sleeve;
   an elongate member slidably received within the lumen of the sleeve;
   a flexible distal extension with a first opening, the flexible distal extension being coupled to the sleeve; and
   a tether encircling a specific portion of the first opening of the flexible distal extension, wherein a first end of the tether is coupled to the sleeve, wherein a portion of a second end of the tether passes through the first hole and around the elongate member, and wherein the elongate member is configured to hold the second end of the tether against the sleeve with an interference fit.

14. The apparatus of claim 13, wherein the portion of the second end is partially wrapped around the elongate member.

15. The apparatus of claim 13, wherein the portion of the second end is fully wrapped around the elongate member.

16. The apparatus of claim 13, wherein the portion of the second end exits the first hole after wrapping around a portion of the elongate member.

17. The apparatus of claim 13, wherein the portion of the second end passes through the first hole from outside of the sleeve.

18. The apparatus of claim 13, wherein the portion of the second end passes through the first hole from inside of the sleeve.

19. The apparatus of claim 13, wherein the sleeve further comprises a second hole on the wall of the sleeve, wherein the portion of the second end passes through the first hole from outside of the sleeve and through the second hole from inside of the sleeve.

20. The apparatus of claim 13, wherein the sleeve further comprises a second hole on the wall of the sleeve, wherein the portion of the second end passes through the first hole from inside of the sleeve and through the second hole from outside of the sleeve.

* * * * *